United States Patent
Kehr

(10) Patent No.: US 6,641,531 B2
(45) Date of Patent: Nov. 4, 2003

(54) DEVICE FOR POSITIONING AT LEAST ONE OPTICAL COMPONENT WITHIN AN ENDOSCOPIC SYSTEM

(75) Inventor: Ulrich Kehr, Wurmlingen (DE)

(73) Assignee: Karl Storz GmbH & Co. KG (DE)

( * ) Notice: Subject to any disclaimer, the term of this patent is extended or adjusted under 35 U.S.C. 154(b) by 0 days.

(21) Appl. No.: 09/918,390

(22) Filed: Jul. 30, 2001

(65) Prior Publication Data

US 2002/0049366 A1 Apr. 25, 2002

Related U.S. Application Data

(63) Continuation of application No. PCT/EP00/00659, filed on Jan. 28, 2000.

(30) Foreign Application Priority Data

Jan. 29, 1999 (DE) .......................... 199 03 437

(51) Int. Cl.$^7$ ................................. A61B 1/06
(52) U.S. Cl. ..................... 600/172; 600/181
(58) Field of Search ................ 600/160, 172–177, 600/181

(56) References Cited

U.S. PATENT DOCUMENTS

| | | | | |
|---|---|---|---|---|
| 3,856,000 A | * | 12/1974 | Chikama | 600/173 |
| 4,565,423 A | | 1/1986 | Ueda | 350/171 |
| 4,820,043 A | | 4/1989 | Diener | 356/241 |
| 5,056,902 A | * | 10/1991 | Chinnock et al. | 359/503 |
| 5,575,757 A | * | 11/1996 | Kennedy et al. | 600/167 |
| 6,110,106 A | * | 8/2000 | MacKinnon et al. | 600/181 |

FOREIGN PATENT DOCUMENTS

| DE | 35 15612 C2 | 4/1985 |
|---|---|---|
| DE | 197 13 276 A1 | 3/1997 |
| DE | 199 03 437 C1 | 1/1999 |

\* cited by examiner

*Primary Examiner*—John Mulcahy
(74) *Attorney, Agent, or Firm*—St. Onge Steward Johnston & Reens LLC

(57) ABSTRACT

A device for positioning at least one optical component within an endoscopic system has a housing, through which runs an optical axis, and in which at least one component is arranged. The component is pivotable into the beam path of the endoscopic system about a pivot axis and pivotable out of the beam path. The pivot axis is here arranged running obliquely to the optical axis.

27 Claims, 6 Drawing Sheets

DEVICE FOR POSITIONING AT LEAST ONE OPTICAL COMPONENT WITHIN AN ENDOSCOPIC SYSTEM

CROSS REFERENCE TO PENDING APPLICATION

This application is a continuation of pending International Patent Application PCT/EP00/00659 filed on Jan. 28, 2000, which designates the United States, and which claims priority of German Patent Application 199 03 437.0 filed on Jan. 29, 1999.

BACKGROUND OF THE INVENTION

The invention relates to a device for positioning at least one optical component within an endoscopic system, with a housing, through which runs an optical axis of the endoscopic system and in which the at least one component is arranged, which can be pivoted into the beam path of the endoscopic system about a pivot axis and which can be pivoted out of the beam path.

Such a device is e.g. known from DE-A-197 13 276.

Optical components are understood in the present invention as e.g. lens, filters, field stops and similar equipment, which are used in endoscope optics.

A special application of the present invention is the use of such a device in an endoscopic system for photodynamical diagnosis, photodynamical therapy or for fluorescence diagnosis.

In photodynamic diagnosis, light of a special spectral composition generated in a light source is coupled into the body and directed onto tissue to be examined. Before, a photo sensibilisator or marker material is instilled into the tissue to be examined. By irradiation of the tissue being enriched with the photo sensibilisator with stimulation light, a light-induced reaction is provoked, by which fluorescence radiation from the tissue region to be examined is emitted. There are, to this end, photo sensibilisators, which enrich in tumor tissue stronger than in healthy tissue. By means of the intensity differences of fluorescence radiation it is made possible, in that way, to differentiate tumor tissue from healthy tissue with high contrast. The fluorescence light and the stimulation light are in different spectral regions.

To allow a particularly good observation with high contrast of the tissue to be examined, which observation is free from a background radiation of the stimulation light, which superimposes the observation light, a color filter is brought into the observation beam path, i.e. into the beam path of the fluorescence light, the color filter having a high transmission in the spectral region of the fluorescence light, while its transmission is low in the region of the illuminating light or in the stimulation light. As light sources, also white light sources are often used, wherein a filter is also brought into the illuminating beam path, which has a pronounced transmission in the spectral region of the spectral region that is suitable for the stimulation of the photo sensibilisator.

A beam path is understood in the present invention, thus, as the beam path of illuminating light, which propagates from proximally to distally, and/or of observation light, which propagates from distally to proximally.

As, with the same endoscopic systems, not only an observation of fluorescence light shall be possible, but also a common observation of the tissue region with white light, such color filters need not only as simply as possible to be brought into the beam path, but also to be brought out again.

To this end, filters are known, which can be mounted onto the endoscope, i.e. on its distal end. Such filters are, however, cumbersome to handle. For mounting or detaching of such a filter it is, apart from that, necessary to remove the endoscope, during the diagnosis or therapy, out of the body, which extends the examination or treatment of the patient. Moreover, such mountable filters can easily get lost.

The device known from DE-A-197 13 276 mentioned at the outset for the positioning of components within endoscopic systems has, in an embodiment, a turret wheel, which is rotatable about a housing-centered axis. The turret wheel carries several optical components, which are distributed in a plane and which can be pivoted about the centered axis as the pivot axis into the beam path of the endoscopic system. The pivot axis is arranged eccentrically parallel to the optical axis. This arrangement requires, however, that the optical axis of the endoscopic system must be arranged eccentrically with respect to the housing center axis. In the case of an endoscope, this means that the housing of the device is not arranged concentrically with respect to the endoscope shaft axis, which is, however, desirable.

If the configuration mentioned before was modified in that direction that the housing of the device surrounds concentrically the optical axis of the endoscopic system, the diameter of the housing would have to be enlarged by the double, when the diameter of the turret wheel remains unchanged, the diameter not being able to be reduced in size due to the preset size of the optical components, so that there would be the disadvantage of a radially very bulky device.

SUMMARY OF THE INVENTION

It is, thus, the object of the present invention to improve a device mentioned at the outset in such a way that pivoting in and pivoting out of the at least one optical component within the endoscopic system is possible, without the device being bulky.

The object of the invention is achieved by a device for positioning at least one optical component within an endoscopic system, comprising a housing, in which said at least one optical component is arranged, and through which runs an optical axis of said endoscopic system, a beam path of said endoscopic system extending along said optical axis, wherein said at least one component can be pivoted into said beam path of said endoscopic system about a pivot axis and can be pivoted out of said beam path, wherein said pivot axis is arranged obliquely with respect to said optical axis.

While in the prior art, in particular in the known device, always the concept was maintained to arrange the pivot axis, about which the at least one optical component can be pivoted into and out of the beam path, parallel to the optical axis, it is provided in the invention to arrange the pivot axis obliquely to the optical axis. Pivoting the at least one optical component about a pivot axis, which runs obliquely with respect to the optical axis, equals a folding of the component. Pivoting in and pivoting out the component about a pivot axis, which runs parallel with respect to the optical axis requires namely that the pivot axis runs eccentrically with respect to the optical axis, which always requires a radial minimum construction size of the device. When the one or several components are folded about a pivot axis, which runs obliquely with respect to the optical axis, however, a radially narrow construction can be reached, because the component has to perform no movement in circumferential direction of the housing. In the simplest embodiment, one or several components can be individually mounted pivotably in the housing, e.g. three components in a triangle arrangement seen in cross section at axially equal position, or four components may form e.g. a square arrangement at axially equal position, or individual components can be provided axially one behind the other pivotable about individual own pivot axes. The configuration of the device according to the invention allows in an advantageous manner to arrange the housing, no matter if in round or in square configuration, with reference to the optical axis in such a way that the optical axis transverses approximately centrally through the housing, without that it is necessary to have to configure the housing in large construction to this end. In this way, several components can be arranged in the housing, which in a space-saving way can be respectively individually or together pivoted into the beam path of the endoscopic system and pivoted out of the beam path. A pivot axis arranged obliquely can e.g. be arranged in an angle of 30°, 45°, 60° or 90° or in intermediate angles of these angles with respect to the optical axis, wherein a corresponding arrangement of the optical component with respect to the pivot axis can be chosen, if it is intended for reasons of minimization of the reflection losses and the beam mismatch to have the optical component with its light passage surfaces orthogonal with respect to the optical axis. The device of the invention can advantageously be integrated in an endoscope, wherein then the housing of the device is an integral part of the housing of the endoscope, having the advantage that also the endoscope can be configured with a radially narrow structure in the region of the integrated device.

The object underlying the invention is in that way completely achieved.

In a preferred embodiment the pivot axis is arranged approximately orthogonal with respect to the optical axis.

This measure has the advantage that a simply designed construction of the device is reached, because when the pivot axis runs approximately orthogonal to the optical axis also the relative arrangement between the component and the pivot axis can be chosen as a right angle, in particular for the case mentioned at the outset that for reasons of minimization of the reflection losses and of the beam mismatch a positioning of the component pivoted into the beam path orthogonal with respect to the optical axis is to be reached.

In another preferred embodiment the pivot axis is arranged in such a way that the component in the state pivoted out of the beam path comes in an adjacent position with a flat side of an inner wall of the housing.

By this measure, a particularly space-saving mechanism for pivoting in and pivoting out for the at least one component is created. The housing of the device can be so radially narrow in this embodiment that between the clear diameter provided for the beam path within the endoscopic system and the inner wall of the housing just a gap remains, in which the at least one component in its position pivoted out, i.e. in its resting position, finds enough space. In resting position, the component is then essentially parallel with respect to the optical axis of the endoscopic system. An imaginable simple design is to arrange the pivot axis at an edge of the component and to mount the component like a flap into the housing.

In another preferred embodiment the at least one component is fixed on a carrier, which is fixed at the housing pivotably about the pivot axis, and which is in its cross section configured approximately in L-shape, wherein a first leg of the carrier carries the at least one component, and a second leg is articulatedly fixed at the housing.

It is here advantageous that by means of the carrier a stable holder for the at least one component is provided, which meets the requirements of stableness in permanent operation when pivoting in and out is performed several times. The carrier can in this procedure receive the at least one component of the type of a frame, whereby the component, which is sensitive against mechanical influences is protected on its edge side. The L-shaped configuration of the carrier has the advantage that the carrier can be located in a radially space-saving manner around the beam path in the housing, without interferingly influencing the light passage.

In this procedure, it is preferred if in the housing at least two pivotable carriers are arranged, which each carry at least one component, and which are pivotable independently of each other.

It is here advantageous that with the same device alternatively different components, e.g. two or more optical filters with different spectral transmission characteristics can be alternatively or simultaneously pivoted into or out of the beam path of the endoscopic system.

It is here preferred if the carriers are coupled with each other in such a way that, when the at least one component is pivoted in, the at least one other component is pivoted out, and vice versa.

In this configuration, it is advantageous that a pivot mechanism and/or a flap mechanism is created, which allows an advantageously simple operation. In this embodiment, it can be switched between two or more operating positions by a single actuation mechanism, in which, respectively, e.g. a component is pivoted into the beam path and the other components are pivoted out of the beam path.

In another preferred embodiment the carriers are arranged axially in an approximately same position.

By this measure, not only a radially, but also an axially small device is created. In particular in connection with the L-shaped embodiment of the carriers mentioned before, two of such carriers can be arranged and mounted pivotable in a space-saving way symmetrically to each other in the housing.

Alternatively to that, it is also preferred, however, if the carriers are arranged at axially different positions.

By this measure, the advantage is achieved that two or more components can be simultaneously pivoted into the beam path. For example, the one carrier may carry a field stop, the other carrier may carry a color filter and the third carrier may carry a heat protection filter, which can be simultaneously brought into the beam path axially arranged one behind the other, which can make sense depending on the application of the endoscopic system.

In another preferred embodiment the carrier carries several components which are distributed in pivot direction over the circumference.

In this embodiment only one pivotable carrier is provided, by which alternatively individual optical components can be pivoted into the beam path and out of the beam path, whereby advantageously with only one carrier several components can be arranged pivotably in the housing, which advantageously means a reduction of the number of parts of the device. In such an embodiment of the carrier, the pivot coupling mentioned before is also achieved, in such a way that, when the at least one component is pivoted in, the other component or the other components are automatically pivoted out of the beam path.

In another preferred embodiment for actuating pivoting in and pivoting out the at least one component, a magnetic coupling is provided, which has at least one outer movable magnetically active element arranged outside the housing or a magnet and at least one inner magnetically active element arranged within the housing, wherein the outer magnetically active element or the outer magnet and the inner magnetically active element coact through the housing via a magnetic frictional connection.

This magnetic coupling known per se for such devices has, again, the advantage that the housing of the device can be configured hermetically tight closed, whereby the advantage is achieved that the device and, thus, the endoscopic device at which the device is provided, can withstand the conditions in an autoclave, so that it is guaranteed that the device can be cleaned as is required for medical purposes. If it is talked about outer magnets in the following, these can also be replaced by magnetically active elements made of magnetic materials like soft-iron cores, at least in the case when magnets are provided as inner magnetically active elements.

In another preferred embodiment the carrier is configured as a two-armed lever with respect to the pivot axis, the one lever arm of which carries the at least one component, and on the other lever arm of which engages an essentially axially movable force transmission element.

In connection with the pivot axis running obliquely to the optical axis, an actuation mechanism is produced via this lever mechanism with an axially movable force transmission element in connection with the carrier configured as two-armed lever, which actuation mechanism is simple in design for pivoting in and out the at least one component.

It is further preferred if the at least one outer magnet or the at least one inner magnetically active element of the magnetic coupling mentioned before are axially movable, wherein the inner magnet is connected to the force transmission element.

This embodiment of the magnetic coupling differs insofar from the magnetic coupling of the known device, as in the latter both the at least one outer magnet and the at least one inner magnet are configured in a rotatable, but axially not movable way. Different from that, in the present invention the advantage is achieved that in connection with the lever mechanism mentioned before, the movement transmission mechanism from the outer magnet as control unit on the lever mechanism is particularly simple in design because no mechanical components need to be provided in the device, to change a rotation movement of the magnets into an axial movement of the lever mechanism. Thus, the expenditure in design of the device of the invention is considerably reduced.

In another preferred embodiment the magnetic coupling comprises at least two outer magnets, which are arranged on a rotatable ring, in axially different positions, wherein the at least one inner magnetically active element is axially movable and connected to the force transmission element, and wherein the two outer magnetically active elements or magnets can alternatively be brought in magnetic engagement with the inner element by rotating the ring.

It is advantageous herein that further a constructively simple magnetic coupling is created, for which, moreover, no mechanical components need to be provided to change a rotation movement into an axial movement. By the rotation easy to be operated of the outer rotatable ring, which is preferably arranged axially immovable around the housing, an axial to-and-fro movement of the inner magnetically active element is caused by alternative engagement of one of the two outer magnets with the one inner magnetically active element because the two outer magnets are arranged at axially different positions.

In another preferred embodiment the at least one inner magnetically active element is arranged on the carrier itself and coacts directly with the at least one outer magnet for pivoting in and for pivoting out of the at least one component.

In this embodiment of the magnetic coupling there is the advantage that for folding down the carrier, which carries the at least one component, no further force transmission elements are necessary, whereby the construction of the magnetic coupling is further simplified in design and, in addition to that, the danger of functional defects is reduced due to the smaller number of movable parts.

It is here, again, preferred when the at least one outer magnet is movable via a rotatable ring surrounding the housing.

By this measure, again, a simple actuation mechanism for the magnetic coupling is created, by which the at least one component can be pivoted into and out of the beam path in a manner that is easy to operate.

In another preferred embodiment two inner magnetically active elements are arranged, in the form of two magnets, on carriers, wherein the inner magnets, with respect to the pivot axis, are arranged opposite to each other and polarized opposite to each other, and that at least two outer magnets are arranged outside the housing, which are, alternately, movable into a position, in which they coact magnetically with the inner magnets, in order to pivot in and out the at least one component.

This represents a preferred and advantageous embodiment of a magnetic coupling with magnetic elements that are arranged directly at the carrier, in which the turning of the carrier for pivoting in and out is performed by at least two magnetic fields which are opposite directed. Due to the arrangement of the two inner permanent magnets in opposite with respect to the pivot axis, each time, when the at least one other of the outer magnets is brought magnetically into engagement with the two inner permanent magnets, a torque is created that moves the carrier from its previous position, e.g. the position pivoted in, into another position, i.e. then into the position pivoted out.

For the embodiments mentioned before, in which the at least one outer magnet is arranged on a rotatable ring, which serves as actuation element or as operation element for pivoting in and out the at least one component, it is further preferred when this ring has at least two lock-in positions, wherein at least a first lock-in position is assigned to a pivoted out position of the component and at least a second lock-in position is assigned to a pivoted in position of the component.

By means of such lock-in positions in which the ring locks in an audible or noticeable way, the user can decide how far to rotate the ring to arrive from the position pivoted in of the at least one component into the position pivoted out. If a mark is applied on the ring, he can, apart from that, always determine the position of the at least one component.

In another preferred embodiment the at least one outer magnet is a permanent magnet.

The use of a permanent magnet has the advantage that the magnetic coupling can be constructed particularly simple, in particular, no current supplies are required as for electric magnets.

In another preferred embodiment the at least one outer magnet is an electric magnet, wherein the at least one inner magnetically acting element is connected to a back-force spring, if necessary.

The use of an electric magnet for the magnetic coupling is also advantageous because pivoting in and out the optical component can be performed by changing the current direction in the electric coil without an outer regulating unit at the housing of the device being necessary. If necessary, the inner magnetically active element can be connected to a back-force spring and, thus, be pre-stressed in an end position, so that pivoting in and out the component is not performed via changing the current direction, but only by switching on and off the current supply into the electric coil.

In another preferred embodiment the at least one inner magnetically active element is a magnet or a soft-iron core.

In another preferred embodiment a moving coil drive with an electric coil and an anchor is arranged in the inner part of the housing, the anchor being arranged therein axially movable and being connected to the force transmission element.

In this embodiment is, thus, no magnetic coupling acting from the outside through the housing to the inward is provided, but as an actuation device for pivoting in and out the optical component in the inner part a moving coil drive, i.e. an electric coil is arranged, in which an anchor, e.g. a magnet or a soft-iron core is arranged axially movable. The electric coil must then, however, be supplied with current from the outside through the housing. By changing the current direction, the anchor connected to the force transmission element is axially moved to-and-fro, whereby then the optical component is pivoted in and out. Here, the anchor can also be connected to a back-force spring so that the actuation of the optical component is performed by switching on and off the current. The advantage of this embodiment is a further reduction of the radial dimension of the device, as an outer actuation element at the housing of the device is not necessary. In the inner part, also a double coil with a respective winding for each position of the optical component may be provided, wherein then by corresponding control of the corresponding winding, pivoting in and out of the optical component is actuated.

An endoscope according to the invention, which is particularly used for photodynamical diagnosis, for therapy or for fluorescence diagnosis, has a device according to the invention of the type or types described before.

It is then preferred when the device is arranged at the proximal end of the endoscope in an optical head between the eyepiece lens and the cover glass of the eyepiece.

It is here advantageous that there is enough place for the device at this location of the endoscope, and that the optical component, e.g. a filter, is located far enough from first image planes, so that possible contaminations of the component, e.g. dust particles, are not imaged.

In another preferred embodiment the housing of the device forms the housing of the endoscope.

This measure has the advantage that the housing of the device is an integral part of the endoscope housing, whereby it is made possible to construct the endoscope housing altogether hermetically tight and, apart from that, to construct the endoscope housing itself radially narrow.

In another preferred embodiment the housing is hermetically tight.

It is here advantageous that the endoscope can be sterilized in an autoclave, so that moisture or contaminations cannot enter the inner part of the housing. The hermetically tight embodiment of the housing is, on the one hand, reached by the magnetic coupling, on the other hand, by the construction that is integral with the housing of the endoscope of the device.

Further advantages can be taken from the following description and the enclosed drawings.

It is to be understood that the features mentioned above and those yet to be explained below can be used not only in the respective combinations indicated, but also in other combinations or in isolation, without leaving the scope of the present invention.

BRIEF DESCRIPTION OF THE DRAWINGS

Embodiments of the invention are shown in the drawings and will be explained in more detail in the description below. In the drawings.

DETAILED DESCRIPTION OF THE DRAWINGS

Figure 1:
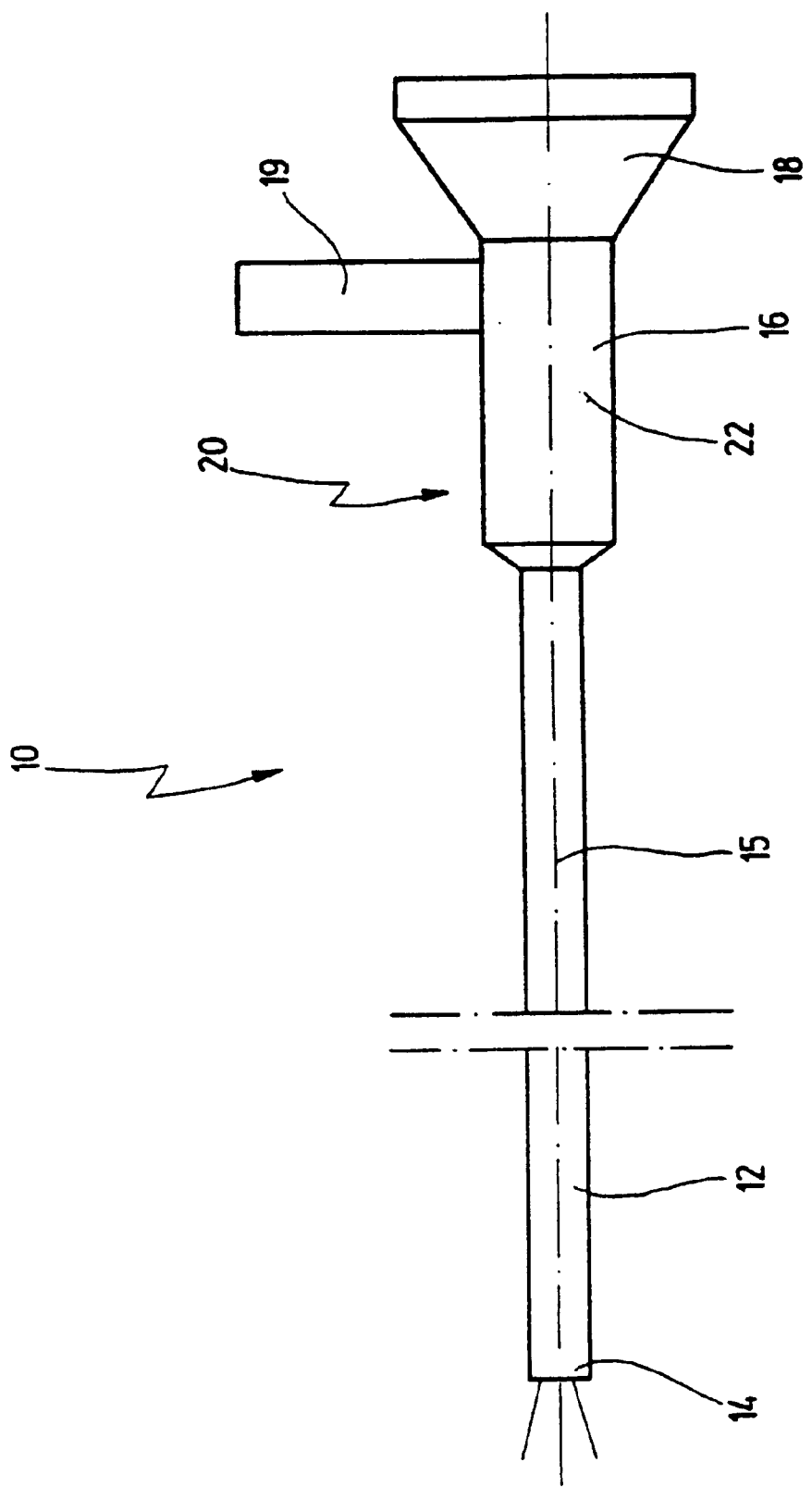
FIG. 1 shows a schematic total representation of an endoscope.

In FIG. 1, an endoscope labeled with the general reference numeral 10 is depicted as an endoscopic system for photodynamical diagnosis and/or for fluorescence diagnosis.

Endoscope 10 has an elongated shaft 12, in which is contained an optical image forming system not shown in detail, which is made of several lenses arranged one behind the other. A distal end 14 of shaft 12 forms the light output sided end for illuminating light and the light input sided end for observation light of the endoscopic system.

An optical axis 15 of the optical system coincides approximately with the longitudinal center axis of shaft 12. An optical head 16 is attached to a proximal end of shaft 12, the optical head carrying at its proximal end an eyepiece cup 18 of an eyepiece.

A light waveguide connection 19 serves for connecting a light conducting cable not shown in order to couple in light that was generated in an external light source not shown into endoscope 10, which then emerges at distal end 14 for illumination of an examination area.

Endoscope 10 has a device 20 according to the invention for positioning at least one optical component within endoscope 10, which is described in detail in the following with reference to FIGS. 2 and 3.

Device 20 has a housing 22, which is configured cylindrically in the embodiment shown. Housing 22 forms at the same time the housing of optical head 16 of endoscope 10 in FIG. 1 and is, thus, an integral part of the housing of endoscope 10.

In housing 22, an optical component 24, e.g. an optical filter, is arranged. Optical axis 15 in FIG. 1 runs approximately centrally through housing 22.

Figure 2:
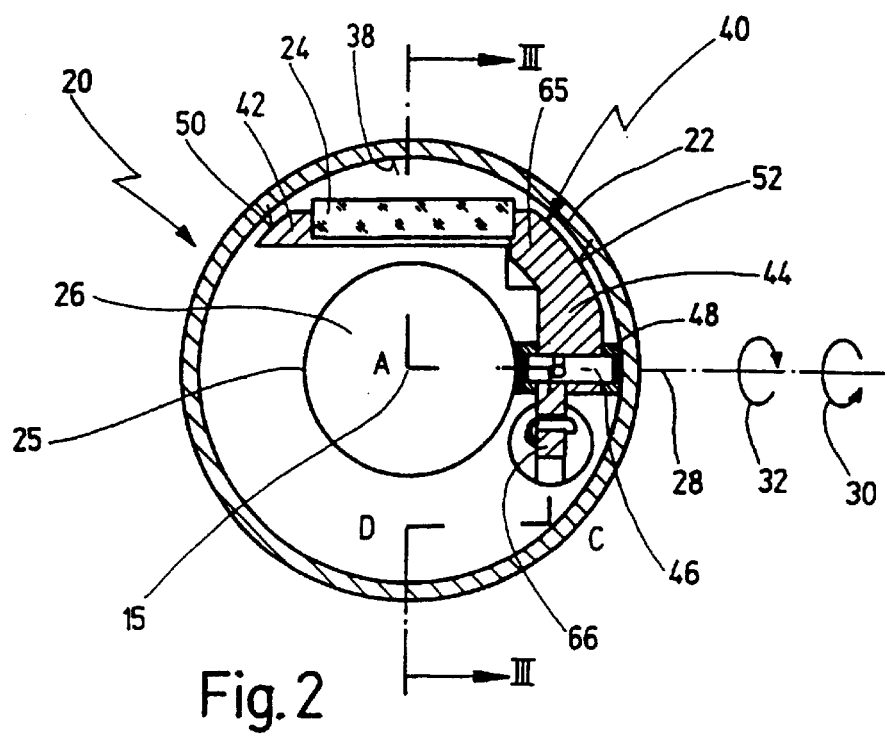
FIG. 2 shows a cross section of a device for positioning at least one optical component within the endoscope.

A circle 25 drawn in FIG. 2, which is concentric with respect to housing 22, encloses a cross-sectional area 26, which represents the cross-sectional area of the beam path of endoscope 10.

Optical component 24 can be pivoted in about a pivot axis 28 into the beam path of endoscope 10 according to an arrow 30 and can be pivoted out of the beam path according to an arrow 32. FIG. 2 and FIG. 3a) show optical component 24 in a state pivoted out of the beam path, while FIG. 3b) shows optical component 24 in a state pivoted into the beam path.

The beam path studied here may be either the beam path of the illuminating light, the light path of which runs from proximally to distally, and also the beam path of the observation light, the light path of which runs from distally to proximally.

In the state pivoted into the beam path, light passage sided end surfaces 34 and 36 of optical component 24 run obliquely to the beam path, i.e. obliquely to optical axis 15, and cover in this procedure essentially cross-sectional area 26 of the beam path.

In the state pivoted out of the beam path according to FIG. 3a), light passage sided end surface 34 of an inner wall 38 is adjacent to housing 22. In its state pivoted out, optical component 24 is completely removed from the beam path of endoscope 10.

As can be seen from FIG. 2 and FIGS. 3a) and 3b), pivot axis 28 runs obliquely to optical axis 15. In the embodiment shown, pivot axis 28 runs approximately orthogonally with respect to optical axis 15. Furthermore, pivot axis 28 lies on an imaginary straight line, which intersects optical axis 15. Furthermore, pivot axis 28 lies on a diameter of housing 22.

In the state pivoted out of the beam path, component 24 is located, seen in cross section, between cross-sectional area 26 of the beam path and inner wall 38 of housing 22.

Component 24 is fixed on a carrier 40. Carrier 40 is configured approximately in L-shape in the cross section according to FIG. 2. Carrier 40 has to this end a first leg 42, which carries component 24 in the type of a frame. A second leg 44, which is integrally connected to first leg 42, runs essentially right-angled to first leg 42.

Second leg 44 is articulatedly connected to housing 22 by means of a pivot pin 46, which is rotatably held in a bearing sleeve or fork 48.

Due to the L-shaped configuration of carrier 40, it is guaranteed that legs 42 and 44, neither in the state pivoted in of component 24 according to FIG. 3b) nor in the state pivoted out according to FIG. 2 and FIG. 3a), are no light barriers. In particular, second leg 44 moves, when component 24 is pivoted in and out, always along inner wall 38 of housing 22, without passing through the beam path. Outer sides 50 of first leg 42 and 52 of second leg 44 are, for the sake of saving space, adjusted to the contour of inner wall 38 of housing 22.

For actuating pivoting in and out of component 24 into the beam path and out of the beam path, device 20 further has a magnetic coupling 54.

Magnetic coupling 54 has at least one outer movable magnet 56, which is arranged outside housing 22, the magnet being represented in FIGS. 3a) and 3b) only very schematically.

Magnetic coupling 54 has further at least one inner movable magnetically active element 58 that is arranged within housing 22 and that is also represented only schematically. The at least one outer magnet 56 and the at least one inner magnetically active element 58 act together through housing 22 by a magnetic force, i.e. a movement of outer magnet 56 causes a movement directed in the same direction of inner element 58. By providing magnetic coupling 54 for actuating pivoting and out of component 24, housing 22 is preferably configured hermetically tight, i.e. it has no openings that would have to be provided in the case of a purely mechanically acting actuation mechanism, in order to transmit a movement of a control unit arranged outside housing 22 passing through housing 22 onto a mechanical control unit or a force transmission element arranged in housing 22.

The at least one outer magnet 56 and the at least one inner magnetically active element 58 are, according to double arrows 60 and 62, magnetically coupled to each other and axially movable.

Inner element 58 is held, to this end, in a guide sleeve 64, which is arranged outside cross-sectional area 26 of the beam path, so that the beam path is not impaired by guide sleeve 64. Outer magnet 56 opposite with respect to inner element 58 can be fixed on the inner side of a sleeve that is movably arranged around housing 22, this sleeve not being shown in detail serves as an actuation element for the user in form of a slide.

The at least one inner magnetically active element 58 is e.g. a magnet in form of a permanent magnet or a soft-iron core.

The at least one outer magnet 56 is a permanent magnet, but can also be, however, an electric magnet.

Instead of the arrangement mentioned before, in which the at least one outer magnet 56 and the at least one inner magnetically active element 58 are axially movable, the magnetic coupling can be, however, configured in such a way that it has at least two outer magnets, which are arranged at axially different positions approximately diametrically opposite at a rotatable ring, the at least one inner magnetically active element 58 further being axially movable, so that then the two outer magnets can alternatively be brought in engagement with inner element 58 by rotating the ring, to be more precise, alternating.

Carrier 40 is further configured as a two-armed lever, wherein a first lever arm 65, which is formed by legs 44 and 42, carries component 24, and on another lever arm 66 a force transmission element 68 is articulated in form of a pull and a push rod. Force transmission element 68 is, to this end, articulated on inner magnetically active element 58 with its end 70 opposite with respect to second lever arm 66. In that way, a lever mechanism is created for pivoting carrier 40 and, thus, for pivoting component 24 about pivot axis 28, which is formed by pivot pin 46.

Starting out from FIG. 3a), which shows component 24 in the state pivoted out of the beam path, by moving outer magnet 56 into the direction of an arrow 72, also inner element 58 is moved into the direction of arrow 72, wherein the movement of inner element 58 is transmitted onto second lever arm 66 of carrier 40 via force transmission element 68, whereby carrier 40 is pivoted into the direction of an arrow 73 into the position shown in FIG. 3b), in which component 24 is pivoted into the beam path of endoscope 10. Starting out from the position of component 24 in FIG. 3b), this component is pivoted out of the beam path by moving outer magnet 56 in the direction of an arrow 74.

In the case of the embodiment of the magnetic coupling mentioned before, in which at least two outer magnets are provided, which act together with at least one inner axially movable magnetically active element 58, wherein the two outer magnets are arranged at axially different positions and approximately diametrically opposite, the following functioning is established. If, by rotating the ring, the axially right magnet is magnetically brought in engagement with inner element 58, inner element 58 is moved to the right according to arrow 60, whereby component 24 is folded out of the beam path. If, by further turning the ring about approximately 180°, the left outer magnet is magnetically brought in engagement with inner element 58, inner element 58 is moved to the left according to arrow 60 in FIG. 3a), whereby component 24 is folded into the beam path. By rotating the ring, it can, thus, be switched between the two pivot end positions according to FIGS. 3a) and 3b).

Another embodiment of the magnetic coupling described before can be that the outer magnet is configured in form of an electric magnet instead of a permanent magnet, i.e. that it has an electric coil, which is suitably supplied with current. By changing the current direction, inner magnetically active element 58 can then be moved to-and-fro for pivoting in and out optical component 24. Inner magnetically active element 58 can also be prestressed by a backforce spring in one of its end positions, so that moving to-and-fro element 58 is caused by switching on and off the current in the electric coil.

Instead of the magnetic couplings described before, a moving coil drive arranged in housing 22 can alternatively be provided, which has a moving coil, i.e. an electric coil, in which an anchor, e.g. a magnet or a softiron core is axially movably arranged. The armature is then connected to force transmission element 68 in force-locking manner. By suitable supply with current, the anchor may then be moved to-and-fro in order to cause pivoting in and out of optical component 24.

In this embodiment of the actuation mechanism, an outer magnet is not necessary, so that the device can be radially constructed particularly narrow. In the inner part of housing 22, also a double coil may be arranged, which each has a winding for each position of optical component 24, which are then suitably supplied with current for pivoting in and out component 24.

Carrier 40 further has a stop 76, which is formed by a corresponding abutment surface on first leg 42 of carrier 40, the abutment surface coming in contact with a component 77 firmly connected to housing 22 of device 20 in the state of component 24 pivoted out of the beam path. In the state pivoted into the beam path of component 24, second leg 44 of carrier 40 further forms a stop 78, which comes in contact with guide sleeve 64. In that way, the two pivot end positions of component 24 are well defined by stops 76 and 78. In particular, stop 78 guarantees in the state pivoted into the beam path of component 24, that component 24 always occupies the same position that is required for the light passage with reference to the optical axis, so that undesired wrong positions of component 24 in the optical system are avoided.

Figure 4:
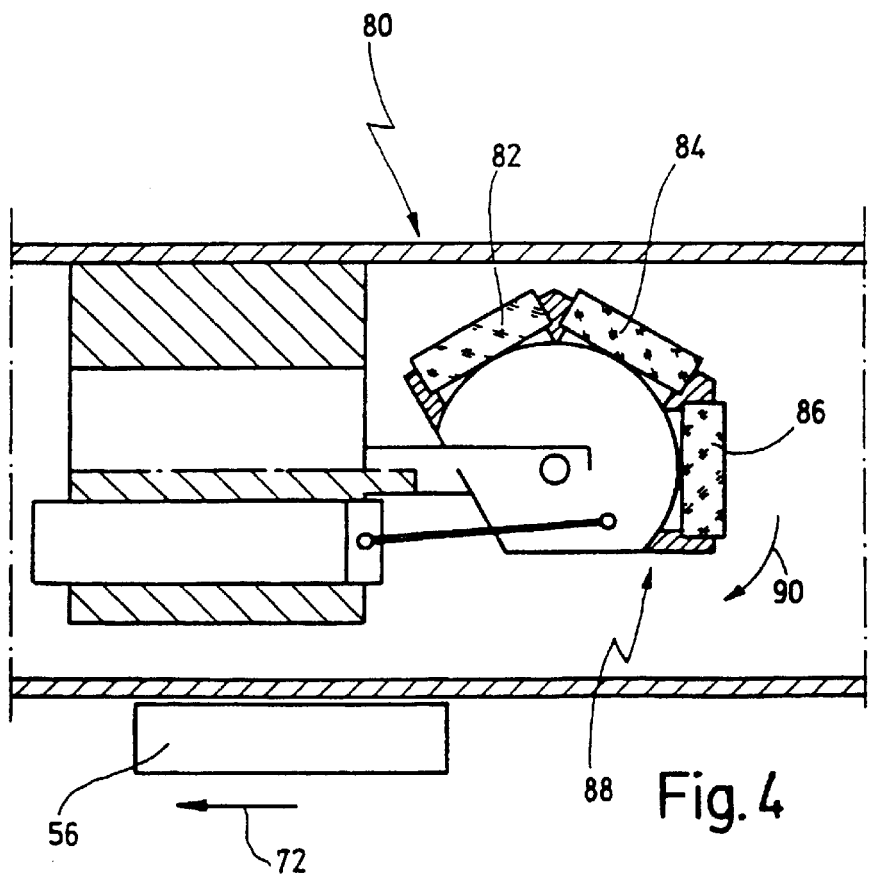
FIG. 4 shows a section according to FIGS. 3a) and 3b) of another device according to another embodiment.

In FIG. 4, according to another embodiment, a device 80 for positioning several optical components 82, 84, 86 is depicted, which can also be used in endoscope 10 in FIG. 1. The same parts as in device 20 are labeled with the same reference numerals.

Figure 3:
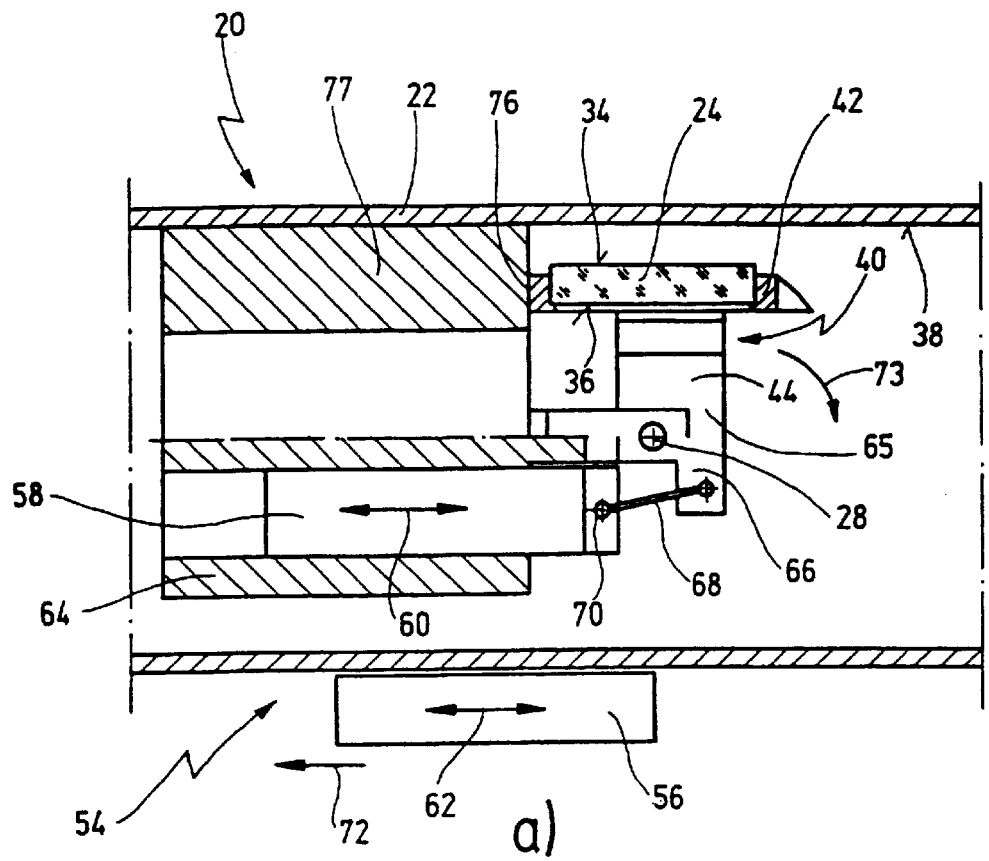
FIGS. 3a) and 3b) show a section of the device in FIG. 2 along line III-A-B-C-D-III in FIG. 2, wherein FIG. 3a) shows the device in a first operating position and FIG. 3b) shows the device in a second operating position.
Figure 3:
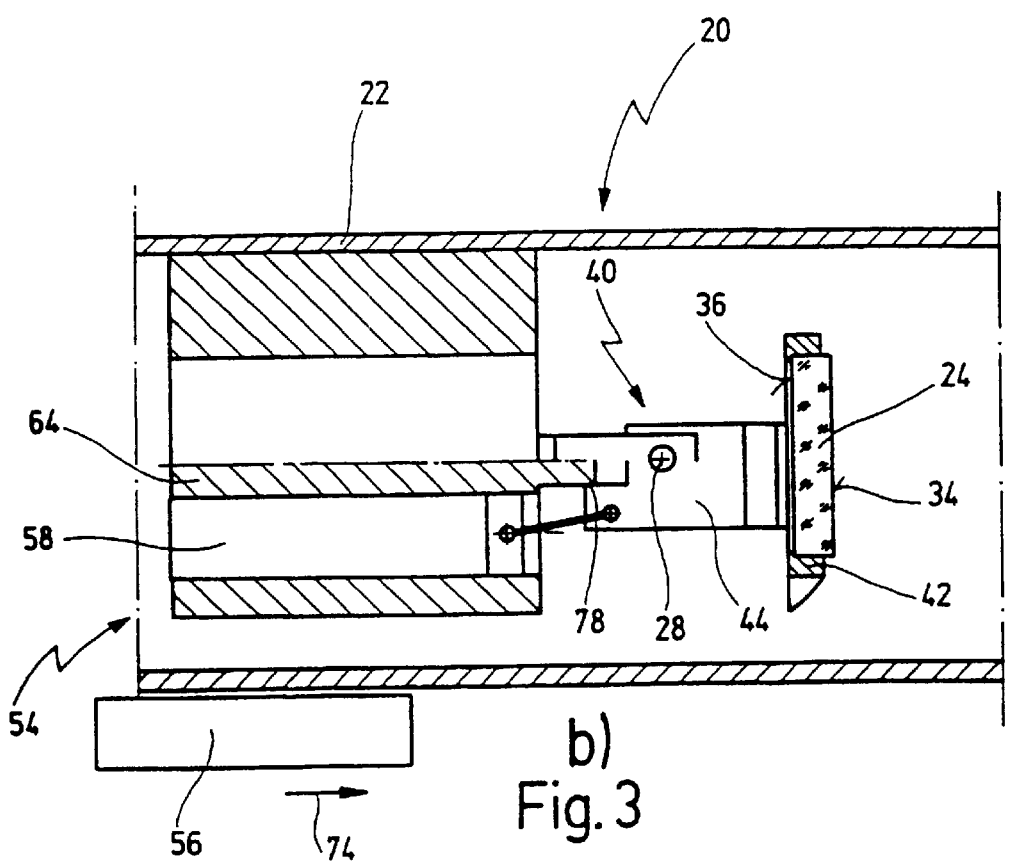

As an essential difference to device 20 according to FIGS. 2 and 3, device 80 has a carrier 88 that is modified compared to carrier 40, carrier 88 carrying components 82, 84, 86. While carrier 88 is, again, configured in L-shape in its cross section, carrier 88 carries the three components 82, 84, 86, which are circumferentially distributed in pivot direction and which can be alternatively pivoted in and out of the beam path of endoscope 10. Components 82, 84, 86 can be e.g. several optical filters with different spectral transmission factors or e.g. a color filter, a lens and a heat protection filter.

In the illustration according to FIG. 1, component 86 is pivoted into the beam path of endoscope 10. By moving outer magnet 56 in direction of arrow 72, component 86 is pivoted out of the beam path in direction of an arrow 90, whereby, automatically coupled with it, component 84 is pivoted into the beam path. If outer magnet 56 is pivoted out of the beam path in direction of arrow 72, component 84 is pivoted out of the beam path, while component 82 is pivoted into the beam path in this movement. With such a configuration of device 80, alternatively one of components 82, 84, 86 can be pivoted into the beam path.

Figure 5:
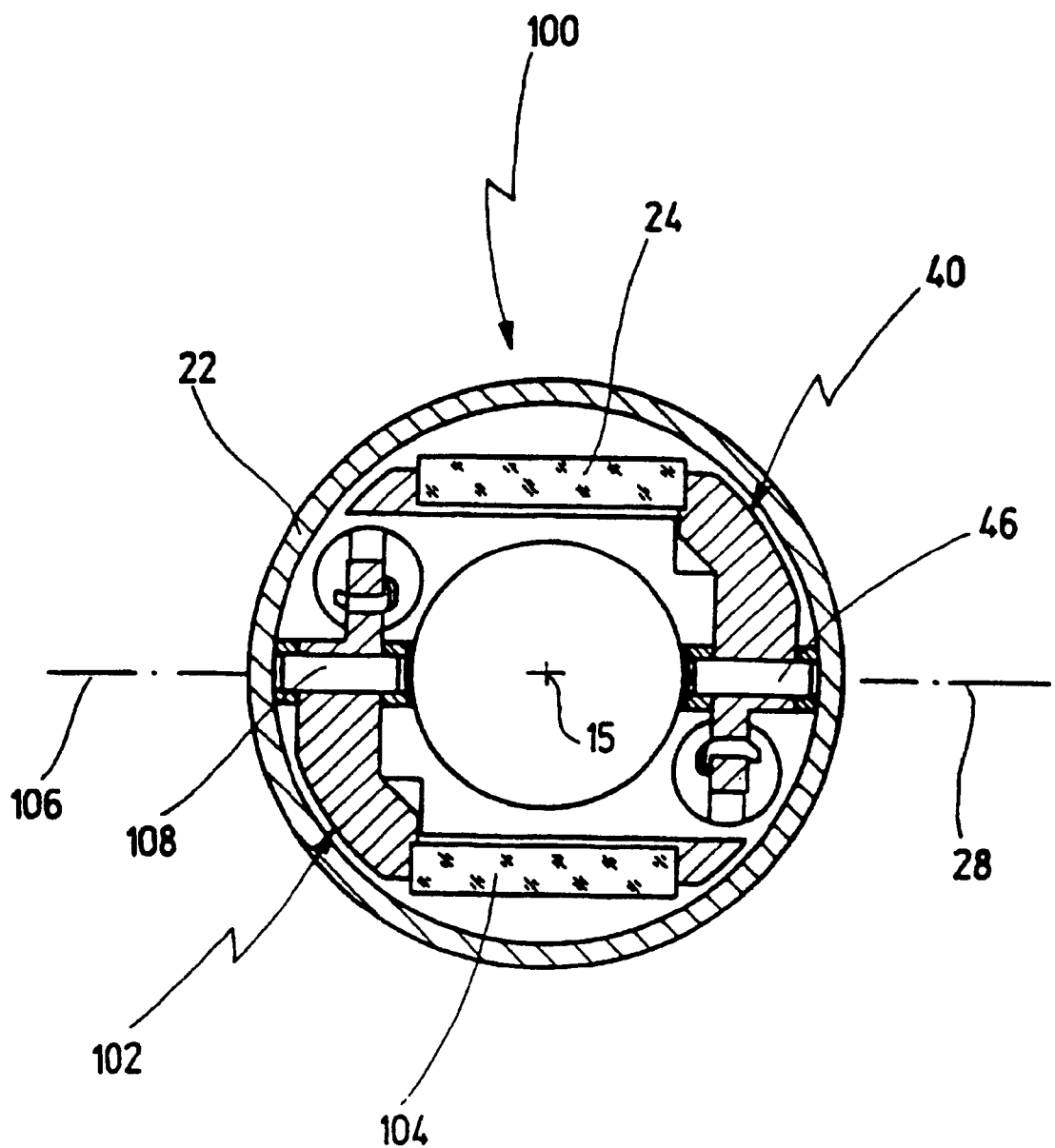
FIG. 5 shows a cross section according to FIG. 2 of another device according to still another embodiment.

In FIG. 5, finally, another embodiment of a device 100 for use in endoscope 10 is shown. Device 100 represents a modification of device 20 according to FIGS. 2 and 3, wherein again, in device 20, the same parts are labeled with same reference numerals.

Additionally to carrier 40, which carries component 24, device 100 has a second carrier 102, which carries another component. Carrier 40 and carrier 102 are configured identically to each other, however, arranged mirror-symmetrically to each other. Carrier 102 and, thus, a further component 104 is pivotable into and out of the beam path of endoscope 10 about a further pivot axis 106, which runs obliquely to optical axis 15. Pivot axis 106 is formed by a pivot pin 108.

In the embodiment shown according to FIG. 5, carrier 40 and carrier 102 are axially arranged in the same position, so that component 24 and alternatively component 104 can be pivoted into the beam path. For pivoting carrier 102, again, a magnetic coupling may be provided, wherein another outer magnet and another magnetically active element can be arranged diametrically opposite to outer magnet 56 and inner magnetically active element 58 according to FIG. 3a). The magnetic coupling can, however, also be configured in such a way that outer magnet 56 according to FIG. 3a) is not only arranged axially movable, but also rotatable, so that for pivoting carrier 102 only one additional inner magnetically active element is provided, wherein outer magnet 56 can, by rotating by 180°, be brought in coacting position alternatively with inner element 58 or with the inner element provided for carrier 102.

Starting out from FIG. 5, it can also be provided to arrange carrier 102 about its pivot axis 106 with respect to carrier 40 by 90° pivoted and to rigidly couple pivot pin 108 of carrier 102 with pivot pin 46 of carrier 40, so that magnetic coupling 54 according to FIG. 3a) with only one outer magnet 56 and only one inner element 58 is sufficient for pivoting component 24 or component 104 alternatively into the beam path or out of the beam path.

Instead of arranging carrier 102 and carrier 40 axially in the same position in housing 22, it can also be advantageous to arrange these axially in different positions and to configure them independently of each other pivotable about pivot axis 28 and/or about pivot axis 106. In this case, component 24 and component 104 can be commonly pivoted into the beam path. Component 24 can be e.g. a color filter and component 104 a heat protection filter, a light stop or lens.

Figure 6:
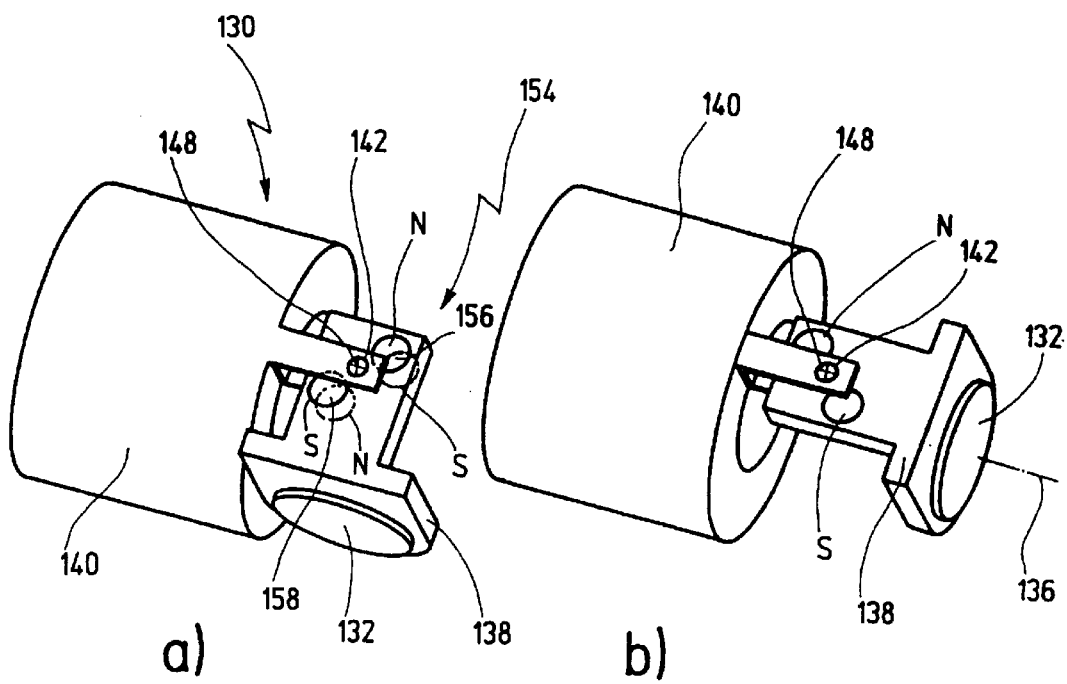
FIGS. 6a) to 6d) show a device for positioning at least one component according to another embodiment in schematically simplified perspective representations, which illustrate the functioning of the device.
Figure 6:
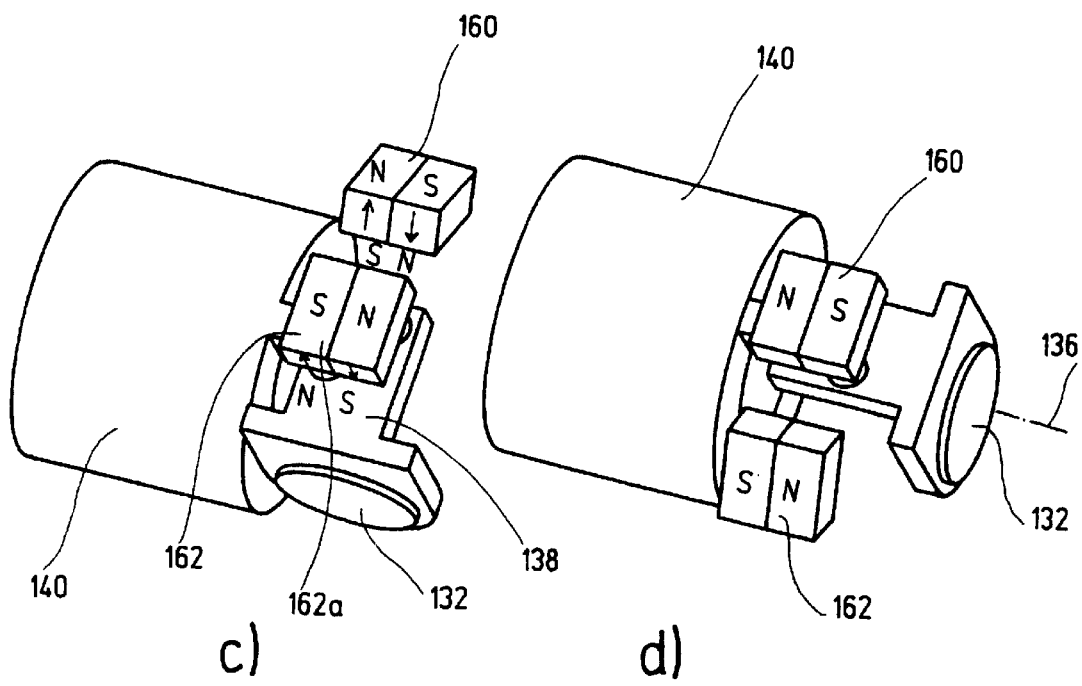

In FIGS. 6a) through d), another embodiment of a device labeled with the general reference numeral 130 for positioning at least one optical component 132 is shown, wherein device 130 can also be used in endoscope 10.

Optical component 132 is shown in FIGS. 6b) and d) in a state pivoted into the beam path of the endoscope that is not shown, so that the optical axis designated with 136 passes through optical component 132.

Optical component 132 can be pivoted into and out of the beam path of the endoscope.

Optical component 132 is mounted on a carrier 138, which is pivotably mounted on a holder 140 by means of a pin 142. Holder 140 is fixed in the endoscope not shown in its optical head.

In a manner comparable to FIG. 5, holder 140 can also hold two carriers in order to take up pivotably two optical components.

Pin 142 defines a pivot axis 148, about which optical component 132 is pivotable into and out of the beam path of endoscope 120.

Carrier 138 is configured in L-shape in its cross section.

Pivot axis 148 runs obliquely, according to the embodiment shown in FIGS. 6a) and d) vertically to optical axis 136.

Device 130 for positioning optical component 132 has a housing that is not shown, which is at the same time the housing of the optical head of the endoscope. The housing, again, is hermetically tight.

For pivoting in and out optical component 132, a magnetic coupling 154 is provided. Magnetic coupling 154 is different from magnetic coupling 54 according to FIG. 3 in that a force transmission element like force transmission element 68 in FIG. 3a is not necessary for magnetic coupling 154. Magnetic coupling 154 is, rather, configured in such a way, as will be described in more detail in the following, that the magnetic action of at least one outer magnet on carrier 138 occurs directly in order to fold same down.

This is illustrated by means of FIGS. 6a) through 6d).

Carrier 138 is shown in FIGS. 6a) and 6c) in a position in which optical component 132 is pivoted out of the beam path of the endoscope, and in FIGS. 6b) and 6d) in a position, in which optical component 132 is pivoted into the beam path of the endoscope.

Magnetic coupling 154 comprises two inner magnetically active elements 156 and 158 in form of permanent magnets.

As can be taken from FIG. 6a), magnetically active elements 156 and 158 are each configured as cylindrical rod magnets, which are let in carrier 138.

Magnetically active element 156 is arranged diametrically opposite to magnetically active element 158 with reference to pivot axis 148 defined by pin 142 and oppositely polarized.

To this end, in both magnetically active elements 156 and 158, the North Pole is designated as N and the South Pole as S.

Magnetic coupling 154 has further at least one, in the embodiment shown two outer magnets 160 and 162, which have been omitted in FIGS. 6a) and b). Outer magnets 160 and 162 are each configured as magnet pairs. Again, the North Pole was depicted as N and the South Pole as S of the magnetically acting magnet elements.

Outer magnets 160 and 162 are fixed on a rotatable ring not shown, which surrounds the housing of device 130.

By rotating the ring, now, outer magnet 160 or outer magnet 162 can be brought in engagement with inner magnetic elements 156 and 158.

FIG. 6c) shows, by omitting the rotatable ring, a rotation position, in which outer magnet 162 is magnetically in engagement with magnetically active elements 156 and 158. In this constellation, carrier 138 takes a position, in which South Pole S of magnetically active element 158 is opposite to the North Pole of magnet element 162a of outer magnet 162.

If the ring remains in this rotation position, carrier 138 is retained in this pivot position, with optical component 132 pivoted out of the beam path in the position depicted in FIG. 6c) because of the magnetically attracting action between the magnetic field of magnet element 162a and magnetically active element 158.

If the ring is rotated so far, starting out from this position, that outer magnet 160 is opposite to magnetically acting elements 156 and 158, outer magnet 160 exerts a torque with respect to pivot axis 148, with the effect that carrier 138 pivots about pivot axis 148 and takes its position shown in FIG. 6d). In this case, optical component 132 is pivoted into the beam path of endoscope 120.

By rotating back the ring, starting out from FIG. 6d), the position depicted in FIG. 6c) of carrier 138 is again adjusted. By rotating the ring to-and-fro, thus, component 132 can be folded over between the position pivoted in and pivoted out.

In FIGS. 7a) and 7b), in a slight modification in comparison to FIGS. 6a) through 6d), is represented that outer magnets 160' and 162' are not configured as magnet pairs, but as individual magnets, wherein, again, the South Pole is indicated with S and the North Pole of magnets 160' and 162' is indicated with N. The positioning of inner magnetically active elements 156 and 158 on carrier 138 is identical with the one in FIG. 6a).

The functioning of magnetic coupling 154' is the same as the one of magnetic coupling 154.

It is further provided for device 130 that the ring already mentioned has at least two lock-in positions wherein at least one lock-in position is assigned to a pivoted out position of component 132 and at least one lock-in position is assigned to a pivoted in position of component 132.

These different lock-in positions are e.g. made possible by a ball lock, which is arranged in the ring, and which acts together with corresponding index notches at the housing, which are configured at the housing circumferentially distributed.

Figure 7:
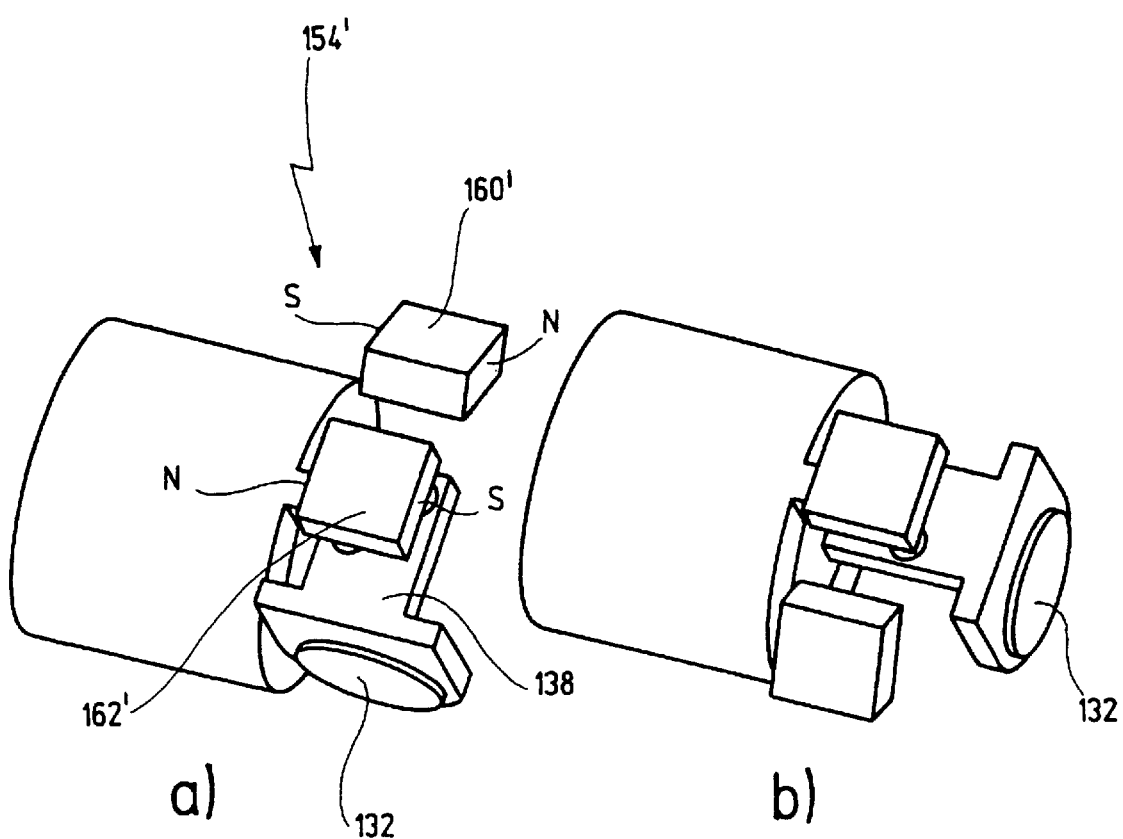
FIGS. 7a) and 7b) show representations corresponding to FIGS. 6c) and 6d) of an embodiment of a device, the embodiment being slightly modified with respect to FIG. 6 for positioning at least one optical component.

In modifications of the embodiment according to FIGS. 7 and 8, two inner magnet elements 156 and 158 can also be replaced by a single magnet, e.g. a rod magnet, which is suitably positioned in carrier 138 and/or 144.

Outer magnets 160 and 162 and 160' and 162' can be replaced by an electric magnet or a soft-iron core, which can be arranged outside or inside housing 152.

What is claimed is:

1. A device for positioning at least two optical components within an endoscopic system, comprising a housing, in which said optical components are arranged, and through which runs an optical axis of said endoscopic system, a beam path of said endoscopic system extending along said optical axis, wherein said components can be pivoted into said beam path of said endoscopic system about a pivot axis and can be pivoted out of said beam path, wherein said pivot axis is arranged obliquely with respect to said optical axis, and wherein at least two pivotable carriers are provided, which each carry at least one of said optical components, and which carriers are pivotable independently of each other, and wherein said carriers are arranged axially in an approximately same position.

2. The device of claim 1, wherein said pivot axis is arranged approximately orthogonal with respect to said optical axis.

3. The device of claim 1, wherein said pivot axis is arranged in such a way that at least one of said components in the state pivoted out of said beam path comes in an adjacent position with a flat side of an inner wall of said housing.

4. The device of claim 1, wherein at least one of said components is fixed on a carrier, which is fixed at said housing pivotably about said pivot axis.

5. The device of claim 4, wherein said carrier, in cross-section, is configured approximately in L-shape, wherein a first leg of said carrier carries said at least one of said components and a second leg is articulatedly fixed at said housing.

6. The device of claim 1, wherein at least one of said components is fixed on a carrier, which is fixed at said housing pivotably about said pivot axis, and wherein said carrier is configured as a two-armed lever with respect to said pivot axis, one lever arm of which carries the at least one of said components, and on the other lever arm of which engages an essentially axially movable force transmission element.

7. The device of claim 1, wherein for actuating the pivoting in and the pivoting out of at least one of said components a magnetic coupling is provided, which has at least one outer movable magnetically active element arranged outside said housing or at least one magnet and at least one inner magnetically active element arranged within said housing, wherein said outer magnetically active element or said outer magnet and said inner magnetically active element coact through said housing via a magnetic force.

8. The device of claim 1, wherein for actuating the pivoting in and the pivoting out of at least one of said components a magnetic coupling is provided, which has at least one outer movable magnetically active element arranged outside said housing or at least one magnet and at least one inner magnetically active element arranged within said housing, wherein said outer magnetically active element or said outer magnet and said inner magnetically active element coact through said housing via a magnetic force, wherein the at least one of said components is fixed on a carrier, which is fixed at said housing pivotably about said pivot axis, and wherein said carrier is configured as a two-armed lever with respect to said pivot axis, one lever arm of which carries the at least one of said components and on the other lever arm of which engages an essentially axially movable force transmission element, and wherein said at least one magnetically active element for said outer magnet and said at least one inner magnetically active element are axially movable, wherein said inner magnetically active element is connected to said force transmission element.

9. The device of claim 1, wherein for actuating the pivoting in and the pivoting out of at least one of said components a magnetic coupling is provided, which has at least one outer movable magnetically active element arranged outside said housing or at least one magnet and at least one inner magnetically active element arranged within said housing, wherein said outer magnetically active element or said outer magnet and said inner magnetically active element coact through said housing via a magnetic force, wherein the at least one of said components is fixed on a carrier, which is fixed at said housing pivotably about said pivot axis, and wherein said carrier is configured as a two-armed lever with respect to said pivot axis, one lever arm of which carries the at least one of said components, and wherein said magnetic coupling comprises at least two outer magnetically active elements or magnets, which are arranged on a rotatable ring, in axially different positions, wherein said at least one inner magnetically active element is axially movable and connected with said force transmission element, and wherein said two outer magnetically active elements or magnets can alternatively be brought in magnetic engagement with said inner element by rotating said ring.

10. The device of claim 1, wherein at least one of said components is fixed on a carrier, which is fixed at said housing pivotably about said pivot axis, and wherein for actuating the pivoting in and the pivoting out of the at least one of said components a magnetic coupling is provided, which has at least one outer movable magnetically active element arranged outside said housing or at least one magnet and at least one inner magnetically active element arranged within said housing, wherein said outer magnetically active element or said outer magnet and said inner magnetically active element coact through said housing via a magnetic force, and wherein said at least one inner magnetically active element is arranged on said carrier itself and coacts directly with said at least one outer magnetically active element or magnet for pivoting in and for pivoting out the at least one of said components.

11. The device of claim 10, wherein said at least one outer magnetically active element or magnet is movable via a rotatable ring surrounding said housing.

12. The device of claim 1, wherein for actuating the pivoting in and the pivoting out of at least one of said components a magnetic coupling is provided, which has at least one outer movable magnetically active element arranged outside said housing or at least one magnet and at least one inner magnetically active element arranged within said housing, wherein said outer magnetically active element or said outer magnet and said inner magnetically active element coact through said housing via a magnetic force, and wherein two inner magnetically active elements are arranged, in the form of two magnets, on carriers, wherein said inner magnets, with respect to said pivot axis, are arranged opposite to each other and polarized opposite to each other, and wherein at least two outer magnets are arranged outside said housing, which are, alternately, movable into a position, in which they coact magnetically with said inner magnets, in order to pivot in and/or to pivot out the at least one of said components.

13. The device of claim 1, wherein for actuating the pivoting in and the pivoting out of at least one of said components a magnetic coupling is provided, which has at least one outer movable magnetically active element arranged outside said housing or at least one magnet and at least one inner magnetically active element arranged within said housing, wherein said outer magnetically active element or said outer magnet and said inner magnetically active element coact through said housing via a magnetic force, and wherein for actuating the pivoting in and the pivoting out of at least one of said components a magnetic coupling is provided, which has at least one outer movable magnetically active element arranged outside said housing or at least one magnet and at least one inner magnetically active element arranged within said housing, wherein said outer magnetically active element or said outer magnet and said inner magnetically active element coact through said housing via a magnetic force, wherein the at least one of said components is fixed on a carrier, which is fixed at said housing pivotably about said pivot axis, and wherein said carrier is configured as a two-armed lever with respect to said pivot axis, one lever arm of which carries the at least one of said components, and wherein said magnetic coupling comprises at least two outer magnetically active elements or magnets, which are arranged on a rotatable ring in axially different positions, and wherein said two outer magnetically active elements or magnets can alternatively be brought in magnetic engagement with said inner element by rotating said ring, and wherein said ring has at least two lock-in positions, wherein at least a first lock-in position is assigned to a pivoted-out position of said component and at least a second lock-in position is assigned to a pivoted-in position of said component.

14. The device of claim 1, wherein for actuating the pivoting in and the pivoting out of at least one of said component a magnetic coupling is provided, which has at least one outer movable magnetically active element arranged outside said housing or at least one magnet and at least one inner magnetically active element arranged within said housing, wherein said outer magnetically active element or said outer magnet and said inner magnetically active element coact through said housing via a magnetic force, and wherein said at least one outer magnetically active element is a permanent magnet or a soft-iron core.

15. The device of claim 1, wherein for actuating the pivoting in and the pivoting out of at least one of said component a magnetic coupling is provided, which has at least one outer movable magnetically active element arranged outside said housing or at least one magnet and at least one inner magnetically active element arranged within said housing, wherein said outer magnetically active element or said outer magnet and said inner magnetically active element coact through said housing via a magnetic force, and wherein said at least one magnetically active element is an electric magnet, which can also be arranged within said housing, wherein said at least one inner magnetically active element may be connected to a back-force spring.

16. The device of claim 1, wherein for actuating the pivoting in and the pivoting out of at least one of said components a magnetic coupling is provided, which has at least one outer movable magnetically active element arranged outside said housing or at least one magnet and at least one inner magnetically active element arranged within said housing, wherein said outer magnetically active element or said outer magnet and said inner magnetically active element coact through said housing via a magnetic force, and wherein said at least one inner magnetically active element is a magnet or a soft-iron core.

17. The device of claim 1, wherein for actuating the pivoting in and the pivoting out of at least one of said components a magnetic coupling is provided, which has at least one outer movable magnetically active element arranged outside said housing or at least one magnet and at least one inner magnetically active element arranged within said housing, wherein said outer magnetically active element or said outer magnet and said inner magnetically active element coact through said housing via a magnetic force, and wherein the at least one of said components is fixed on a carrier, which is fixed at said housing pivotably about said pivot axis, and wherein said carrier is configured as a two-armed lever with respect to said pivot axis, one lever arm of which carries said at least one component, and on the other lever arm of which engages an essentially axially movable force transmission element, and wherein a moving coil drive with an electric coil and an anchor is arranged in an inner part of said housing, said anchor being arranged therein axially movable and being connected to said force transmission element.

18. A device for positioning at least one optical component within an endoscopic system, comprising a housing, in which said at least one optical component is arranged, and through which runs an optical axis of said endoscopic system, a beam path of said endoscopic system extending along said optical axis, wherein said at least one component can be pivoted into said beam path of said endoscopic system about a pivot axis and can be pivoted out of said beam path, wherein said pivot axis is arranged obliquely with respect to said optical axis, wherein said at least one component is fixed on a carrier, which is fixed at said housing pivotably about said pivot axis, and wherein said carrier, in cross-section, is configured approximately in L-shape, wherein a first leg of said carrier carries said at least one component, and a second leg is articulatedly fixed at said housing.

19. The device of claim 18, said pivot axis is arranged approximately orthogonal with respect to said optical axis.

20. The device of claim 18, wherein said pivot axis is arranged in such a way that said component in the state pivoted out of said beam path comes in an adjacent position with a flat side of an inner wall of said housing.

21. The device of claim 18, wherein in said housing at least two optical components are arranged, and wherein at least two pivotable carriers are provided, which each carry one of said at least two components, and which carriers are pivotable independently of each other.

22. The device of claim 18, wherein in said housing at least two optical components are arranged, and wherein at least two pivotable carriers are provided, which each carry at least one of said two components, and which carriers are pivotable independently of each other, and wherein said carriers are arranged axially in an approximately same position.

23. The device of claim 18, wherein said at least one component is fixed on a carrier, which is fixed at said housing pivotably about said pivot axis, and wherein said carrier is configured as a two-armed lever with respect to said pivot axis, one lever arm of which carries said at least one component, and on the other lever arm of which engages an essentially axially movable force transmission element.

24. The device of claim 18, wherein for actuating the pivoting in and the pivoting out of said at least one component a magnetic coupling is provided, which has at least one outer movable magnetically active element arranged outside said housing or at least one magnet and at least one inner magnetically active element arranged within said housing, wherein said outer magnetically active element or said outer magnet and said inner magnetically active element coact through said housing via a magnetic force.

25. The device of claim 18, wherein for actuating the pivoting in and the pivoting out of said at least one component a magnetic coupling is provided, which has at least one outer movable magnetically active element arranged outside said housing or at least one magnet and at least one inner magnetically active element arranged within said housing, wherein said outer magnetically active element or said outer magnet and said inner magnetically active element coact through said housing via a magnetic force, wherein said at least one component is fixed on a carrier, which is fixed at said housing pivotably about said pivot axis, and wherein said carrier is configured as a two-armed lever with respect to said pivot axis, one lever arm of which carries said at least one component, and on the other lever arm of which engages an essentially axially movable force transmission element, and wherein said at least one magnetically active element for said outer magnet and said at least one inner magnetically active element are axially movable, wherein said inner magnetically active element is connected to said force transmission element.

26. The device of claim 18, wherein for actuating the pivoting in and the pivoting out of said at least one component a magnetic coupling is provided, which has at least one outer movable magnetically active element arranged outside said housing or at least one magnet and at least one inner magnetically active element arranged within said housing, wherein said outer magnetically active element or said outer magnet and said inner magnetically active element coact through said housing via a magnetic force, wherein said at least one component is fixed on a carrier, which is fixed at said housing pivotably about said pivot axis, and wherein said carrier is configured as a two-armed lever with respect to said pivot axis, one lever arm of which carries said at least one component, and wherein said magnetic coupling comprises at least two outer magnetically active elements or magnets, which are arranged on a rotatable ring, in axially different positions, wherein said at least one inner magnetically active element is axially movable and connected with said force transmission element, and wherein said two outer magnetically active elements or magnets can alternatively be brought in magnetic engagement with said inner element by rotating said ring.

27. A device for positioning at least one optical component within an endoscopic system, comprising a housing, in which said at least one optical component is arranged, and through which runs an optical axis of said endoscopic system, a beam path of said endoscopic system extending along said optical axis, L(herein said at least one component can be pivoted into said beam path of said endoscopic system about a pivot axis and can be pivoted out of said beam path, wherein said pivot axis is arranged obliquely with respect to said optical axis; and wherein for actuating the pivoting in and the pivoting out of said at least one component a magnetic coupling is provided, which has at least one outer movable magnetically active element arranged outside said housing or at least one magnet and at least one inner magnetically active element arranged within said housing, wherein said outer magnetically active element or said outer magnet and said inner magnetically active element coact through said housing via a magnetic force, wherein said at least one component is fixed on a carrier, which is fixed at said housing pivotably about said pivot axis, and wherein said carrier is configured as a two-armed lever with respect to said pivot axis, one lever arm of which carries said at least one component, and op the other lever arm of which engages an essentially axially movable force transmission element, and wherein said at least one magnetically active element for said outer magnet and said at least one inner magnetically active element are axially movable, wherein said inner magnetically active element is connected to raid force transmission element.

\* \* \* \* \*